US009844566B2

(12) United States Patent
Limonov et al.

(10) Patent No.: US 9,844,566 B2
(45) Date of Patent: Dec. 19, 2017

(54) PHARMACEUTICAL COMPOSITION FOR THE PREPARATION OF INFUSION SOLUTIONS OF ANTIMICROBIAL PREPARATIONS, ITS PRODUCTION PROCESS (VARIATIONS)

(71) Applicant: Viktor Lvovich Limonov, Andorra la Vella (AD)

(72) Inventors: Viktor Lvovich Limonov, Andorra la Vella (AD); Konstantin Valentinovich Gaidul, Novosibirsk (RU); Aleksandr Valerevich Dushkin, Novosibirsk (RU)

(73) Assignee: Viktor Lvovich Limonov, Andorra la Vella (AD)

( * ) Notice: Subject to any disclaimer, the term of this patent is extended or adjusted under 35 U.S.C. 154(b) by 0 days.

(21) Appl. No.: 14/728,136

(22) Filed: Jun. 2, 2015

(65) Prior Publication Data
US 2015/0283172 A1    Oct. 8, 2015

Related U.S. Application Data

(62) Division of application No. 13/650,323, filed on Oct. 12, 2012, now abandoned.

(30) Foreign Application Priority Data

Nov. 22, 2011    (RU) .................................. 2011147170

(51) Int. Cl.
| | |
|---|---|
| *A61K 31/7052* | (2006.01) |
| *A61K 31/7036* | (2006.01) |
| *A61K 31/407* | (2006.01) |
| *A61K 31/02* | (2006.01) |
| *A61K 31/506* | (2006.01) |
| *A61K 31/26* | (2006.01) |
| *A61K 31/14* | (2006.01) |
| *A61K 31/546* | (2006.01) |
| *A61K 33/14* | (2006.01) |
| *A61K 9/00* | (2006.01) |
| *A61K 9/14* | (2006.01) |
| *A61K 38/14* | (2006.01) |
| *A61K 47/02* | (2006.01) |
| *A61K 47/26* | (2006.01) |

(52) U.S. Cl.
CPC ............ *A61K 33/14* (2013.01); *A61K 9/0019* (2013.01); *A61K 9/14* (2013.01); *A61K 9/143* (2013.01); *A61K 9/145* (2013.01); *A61K 31/407* (2013.01); *A61K 31/506* (2013.01); *A61K 31/546* (2013.01); *A61K 31/7036* (2013.01); *A61K 31/7052* (2013.01); *A61K 38/14* (2013.01); *A61K 47/02* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 3,252,859 A | 5/1966 | Silver | |
| 2004/0248778 A1 | 12/2004 | Gloger et al. | |
| 2006/0154069 A1* | 7/2006 | Lin ...................... | A61K 9/0019 428/402 |
| 2013/0164336 A1* | 6/2013 | Limonov .............. | A61K 9/0019 424/400 |
| 2014/0105936 A1 | 4/2014 | Limonov et al. | |

FOREIGN PATENT DOCUMENTS

| | | |
|---|---|---|
| EA | 013864 B1 | 8/2010 |
| EP | 0 470 431 A2 | 2/1992 |
| EP | 0 556 110 A1 | 8/1993 |
| EP | 2 476 419 A1 | 7/2012 |
| JP | S60169431 A | 9/1985 |
| JP | 2001163770 A | 6/2001 |
| RU | 2 333 920 C2 | 9/2008 |
| WO | WO 01/85135 A1 | 11/2001 |
| WO | WO 03/063877 A1 | 8/2003 |
| WO | WO 03/090693 A2 | 11/2003 |
| WO | WO 2005/009602 A2 | 2/2005 |
| WO | WO 2012/0039642 | 3/2012 |

OTHER PUBLICATIONS

Zyvox, Pharmaceutical and Upjohn Company, pp. 1-40 (2008) ([retrieved from on-line website: http://dailymed.nlm.nih.gov/dailymed/archives/fdaDrugInfo.cfm?archiveid=8645, last visit Nov. 3, 2015].*
Seleem et al. (Agents Chemother. 2009, 53 (10), 4270).*
Alexander et al., "Solubility of amorphous siilica in water",Jun. 1954, pp. 453-455.*
Definition of colloidal silica ([retrieved from on-line website: http://www.whatiscolloidal.com/colloidal-silica/ (last visit Nov. 1, 2016]).*
Remington (2006) The Science and Practice of Pharmacy, 21st Edition (Troy ed.) Lippincott Williams & Wilkins, Baltimore, Maryland, United States of America, p. 317.

(Continued)

*Primary Examiner* — Ernst V Arnold
*Assistant Examiner* — Kyung Sook Chang
(74) *Attorney, Agent, or Firm* — Jenkins, Wilson, Taylor & Hunt, P.A.

(57) ABSTRACT

The proposed compositions and methods for preparation thereof relate to pharmacology, medicine, veterinary science and pharmaceutical industry. The compositions can be used for preparing infusion solutions of antimicrobial (antibacterial and antifungal) preparations increasing therapeutic efficiency thereof. The compositions include nanostructured colloidal silica and are efficient when treating overwhelming sepsis of tested animals. The pharmaceutical compositions have a proven and significant clinically important potentiating impact on therapeutic efficiency of the infusion solution, when treating inflammatory diseases, in comparison with traditional solvents.

1 Claim, No Drawings

(56) References Cited

OTHER PUBLICATIONS

Abeylath & Turos (2008) Drug Delivery approaches to overcome bacterial resistance to β-lactam antibiotics. Expert Opinion on Drug Delivery 5(9):931-949.
Bastus et al. (2009) Peptides conjugated to gold nanoparticles induces macrophage activation. Molecular Immunology 46:743-748.
European Search Report corresponding to Application No. Ep 12 18 6239 dated Mar. 13, 2017.
Hamilton et al. (2006) MARCO mediates silica uptake and toxicity in alveolar macrophages from C57BL/6 mice. Journal of Biological Chemistry 281:34218-34226.
Hetrick et al. (2008) Bactericidal efficacy of nitric oxide-releasing silica nanoparticles. ACA Nano 2(2):1-26.
International Preliminary Report on Patentability corresponding to International Application No. PCT/RU2011/000322 dated Mar. 26, 2013.
International Search Report corresponding to International Application No. PCT/RU2011/000322 dated Sep. 29, 2011.
Krishnasami et al. (2002) Management of hemodialysis catheter-related bacteremia with an adjunctive antibiotic lock solution. Kidney International 61:1136-1142.
Langan & Bambeke (2010) Clarithromycin. Kucers' The Use of Antibiotics 6th ed(Chapter 61):779-800.
Li et al (1997) Sulbactam/Cefoperazone Versus Cefotaxime for the Treatment of Moderate-to-Severe Bacterial Infections: Results of a Randomized, Controlled Clinical Trial. Clinical Infectious Diseases 24:498-505.
Lucarelli et al. (2004) Innate defence functions of macrophages can be biased by nano-sized ceramic and metallic particles. European Cytokine Network 15(4):339-346.
Nissen et al. (1986) Fosfomycin-ampicillin versus gentamicin-ampicillin in the treatment of critically ill patients with pneumonia. Infection 14(5):246-249.
Office Action corresponding to Russian Patent Application No. 2011147170/15(070734) dated Jul. 16, 2012.
Office Action (Restriction Requirement) corresponding to U.S. Appl. No. 13/389,652 dated Jun. 5, 2013.
Office Action corresponding to Australian Patent Application No. 2012211402 dated Aug. 30, 2013.
Office Action corresponding to U.S. Appl. No. 13/389,652 dated Oct. 8, 2013.
Office Action corresponding to Japanese Patent Application No. 2012-170753 dated Jan. 7, 2014.
Office Action (Restriction Requirement) corresponding to U.S. Appl. No. 13/650,323 dated Aug. 26, 2014.
Office Action corresponding to U.S. Appl. No. 13/650,323 dated Nov. 18, 2014.
Office Action corresponding to Chinese Patent Application No. 201210260661.9 dated Apr. 11, 2015.
Office Action corresponding to U.S. Appl. No. 13/650,323 dated Aug. 6, 2015.
Office Action corresponding to U.S. Appl. No. 13/389,652 dated Sep. 23, 2015.
Office Action correspondingto Canadian Patent Application No. 2,792,574 dated Jan. 18, 2016.
Office Action corresponding to U.S. Appl. No. 13/650,323 dated Feb. 8, 2016.
Office Action corresponding to U.S. App. No. 13/389,652 dated Jun. 1, 2016.
Office Action corresponding to Chinese Patent Application No. 201210260661.9 dated Jul. 7, 2016.
Office Action corresponding to U.S. Appl. No. 13/650,323 dated July 13, 2016.
Office action corresponding to U.S. Appl. No. 13/389,652 dated May 3, 2017.
Office Action corresponding to Chinese Patent Application No. 201210260661.9 dated Jul. 17, 2017.
Park et al. (2009) Biodegradable luminescent porous silicon nanoparticles for in vivo applications. Nature Materials 8(4):331-336.
Pernis (2005) Silica and the immune system. Acta Biomed 76 Suppl 2:38-44.
Pinto-Alphandary et al. (1994) Intraceullular visualization of ampicillin-loaded nanoparticles in peritoneal macrophages infected in vitro with Salmonella typhimurium. Pharmaceutical Research 11(1):38-46.
Pinto-Alphandary et al. (2000) Targeted delivery of antibiotics using liposomes and nanoparticles: research and applications. International Journal of Antimicrobial Agents 13:155-168.
Rai et al. (2010) Antibiotic mediated synthesis of gold nanoparticles with potent antimicrobial activity and their application in antimicrobial coatings. Journal of Materials Chemistry 20:6789-6798.
Rosemary et al. (2006) Investigation of antibacterial properties of ciprofloxacin@SiO2. Langmuir 22(24):10125-10129.
Snowalter et al (2009) EMSL Quarterly Highlights Report: 2nd Quarter, Fiscal Year 2009. Prepared for the U.S. Department of Energy's Office of Biological and Environmental Research under Contract DE-AC05-76RL01830:1-26.
Tasciotti et al. (2008) Mesoporous silicon particles as a multistage delivery system for imaging and therapeutic applications. Nature Nanotechnology 3:151-157.
Tizim Instruction for medical use Tizim (India) 3 Pages (English Translation of abstract).
Traub (1983) Interactions of antimicrobial drugs and combined phagocytic/serum bactericidal activity of defibrinated human blood against Serratia marcescens. III. beta-Lactam antibiotics and fosfomycin. Chemotherapy 29(1):48-57.
Ulbrich & Lamprech (2010) Targeted drug-delivery approaches by nanoparticulate carriers in the therapy of inflammatory diseases. Journal Royal Society Interface 7(1):555-S66.
Waters et al. (2009) Macrophage responses to silica nanoparticles are highly conserved across particle sizes. Toxicological Sciences 107(2):553-569.
Notification of Transmittal of the International Search Report and the Written Opinion of the International Searching Authority, or the Declaration corresponding to International Application No. PCT/RU2011/000322 dated Sep. 29, 2011.
Zeitlinger et al. (2007) Immunomodulatory effects of fosfomycin in an endotoxin model in human blood. J Antimicrob Chemother 59(21:219-223.
Zolnik et al. (2010) Minireview: Nanoparticles and the immune system. Endocrinology 151(2):458-465.

* cited by examiner

PHARMACEUTICAL COMPOSITION FOR THE PREPARATION OF INFUSION SOLUTIONS OF ANTIMICROBIAL PREPARATIONS, ITS PRODUCTION PROCESS (VARIATIONS)

CROSS-REFERENCE TO RELATED APPLICATIONS

This U.S. patent application is a divisional application of a pending U.S. patent application Ser. No. 13/650,323 filed on 12 Oct. 2012, claiming priority under 35 U.S.C. 119 (a) through (d) from a Russian Federation patent application RU2011147170 filed on 22 Nov. 2011 hereby entirely incorporated by reference.

FIELD OF THE INVENTION

This invention belongs to pharmaceutical preparations suitable for preparing solutions for injectable preparations of antimicrobial pharmaceuticals, and to technologies for compounding thereof; it may be used in medicine and veterinary medicine when treating contagious and inflammatory diseases of different aetiology, as well as in the pharmaceutical industry for producing substances and final dosage forms.

BACKGROUND OF THE INVENTION

Traditionally, during many decades, in clinical practice, for preparing solutions of most antimicrobial (antibacterial and antifungal) preparations for intravenous injections and infusions, the following ingredients are most often used: water solutions for injections, or 0.9% solution of sodium chloride, or 5% solution of dextrose (glucose). The following solutions are used less frequently: 0.45% solution of sodium chloride, 2% and 10% solution of dextrose; Ringer's solution, lactated Ringer's solution, solutions of potassium chloride and sodium chloride for intravenous infusions and some others, which by themselves have no antimicrobial action and do not have a potentiating action for therapeutic efficiency of antimicrobial pharmaceuticals [R-1, see at the end of the present description].

Due to this fact and taking into account the fact that, by the present time, many clinically significant microbial strains have acquired more or less expressed resistibility to many antimicrobial preparations, the elaboration of new original approaches, with the purpose of essential growth of antimicrobial activity and clinical efficiency of many antibacterial and antifungal pharmaceuticals, when treating contagious and inflammatory diseases, is an urgent problem needed to be solved by experimental pharmacology and practical medicine.

Over the last years, it was discovered that the use of various nanoparticles as carriers for delivery of different antibiotics directly to immune system cells is a very promising trend in the development of new pharmaceutical technologies and new efficient methods of the antibiotic therapy [see R-2, R-3, R-4, R-5, R-6, R-7, R-8, and R-9]. It provides for anti-infectious protection of the organism (macrophages), with the purpose of growth of the intracellular concentration of antimicrobial preparations and accordingly the intensification of their antimicrobial properties (which is most important with regard to microorganisms persistent in these cells: clamydias, mycoplasmas, mycobacteria, etc.), as well as for the stimulation of macrophages' antibacterial activity and their additional recruitment into the infected tissues.

OBJECTIVES AND BRIEF DESCRIPTION OF THE INVENTION

A primary objective of this invention is the development of pharmaceutical compositions for preparing infusion solutions made of powder-like injectable forms of antimicrobial preparations on the basis of using sodium chloride, dextrose, and colloidal silica, having a potentiating impact on therapeutic efficiency of the antibacterial and antifungal preparations in comparison with the traditional solvents (water for injection, 0.9% solution of the sodium chloride, 5% solution of dextrose, Ringer's solution, and others) that are considered to be the closest related art compositions, herein also called 'prototypes'). Another objective of the invention is the development of a method for producing the aforesaid pharmaceutical compositions. Other objectives can be found by those skilled in the art upon learning the present disclosure.

The useful result achieved by this invention is the intensification of therapeutic efficiency of parenteral forms of antibacterial and antifungal preparations on the basis of using nanoparticles and microparticles of colloidal silica.

Nanoparticles and microparticles of colloidal silica, differing by pharmacologically advantageous properties of biocompatibility, biodistribution, biodegradation and low toxicity, during the parenteral introduction. They are capable of serving as a carrier of antibiotics for intracellular delivery to macrophages that are typically concentrated in inflammatory tissues in the lungs, liver, kidneys, spleen, lymph nodes, heart, skin, bladder, and other organs of mammals, which considerably increases the concentration of antibiotics at the intracellular level and in infected tissues of the body, and considerably increases the antimicrobial activity of these cells of the immune system (particularly, by means of stimulation of the nitric oxide generation, and activating the phagocytosis process), thereby significantly increasing the therapeutic effect of antibacterial and antifungal pharmaceuticals [see R-10, R-11, R-12, R-13, R-14, R-15, R-16, and R-17].

This problem has been solved by creating the inventive pharmaceutical composition for preparation of infusion solutions of antibacterial and antifungal preparations.

First Variation

A first variation of the inventive pharmaceutical composition is provided for preparing infusion solutions for antimicrobial preparations soluble in sterile water for injections, or in 0.45% solution of sodium chloride, or in 0.9% solution of sodium chloride; this composition is provided in a powder form, and comprises: sodium chloride and colloidal silica, wherein sodium chloride and colloidal silica constitute a weight ratio of 4.5:(1-5) or 9:(1-5), wherein (1-5) is a range of changing the weight from 1 unit to 5 units.

A method for production of the first variation pharmaceutical composition has been developed, wherein the method comprises: —providing sodium chloride in a powder form; —providing colloidal silica in a powder form; —mixing sodium chloride with colloidal silica at a weight ratio of 4.5:(1-5), or 9:(1-5), wherein (1-5) is a range of changing the weight from 1 unit to 5 units, thereby obtaining a mixture characterized by including a mass fraction of fine-dispersed particles of colloidal silica, having dimensions not exceeding 5 micrometers; and—subjecting the so obtained mixture to mechanical processing by means of impacting-abrasive actions, until the aforesaid mass fraction is increased at least twice.

For the preparation of infusion solutions on the basis of using the proposed pharmaceutical composition, a single dose of the dry powder of the antimicrobial preparation (soluble in the water for injection), indicated in the prescribing information, is dissolved in 10 ml of the water for injection, after which the whole volume of the derived solution is carried into the vial with the dry powder of the pharmaceutical composition indicated above, the same is intensively shaken for 2 or 3 minutes, after which the received suspension consisting of the solution of antimicrobial preparation and the pharmaceutical composition is additionally dissolved in 50-100-200 ml of the 0.45% or 0.9% solution of the sodium chloride (depending of the composition contents) and is injected intravenously as an infusion according to the requirements indicated in the antimicrobial preparation prescribing information.

Second Variation

A second variation of the inventive pharmaceutical composition is provided for preparing infusion solutions of antimicrobial preparations soluble in sterile water for injections, or in 2% dextrose solution, or in 5% dextrose solution; this composition is provided in a powder form, and comprises: dextrose and colloidal silica, wherein dextrose and colloidal silica constitute a weight ratio of 20:(1-5) or 50:(1-5), wherein (1-5) is a range of changing the weight from 1 unit to 5 units.

A method for production of the second variation pharmaceutical composition has been developed, wherein the method comprises: —providing dextrose in a powder form; —providing colloidal silica in a powder form; —mixing dextrose with colloidal silica at a weight ratio of 20:(1-5), or 50:(1-5), wherein (1-5) is a range of changing the weight from 1 unit to 5 units, thereby obtaining a mixture characterized by including a mass fraction of fine-dispersed particles of colloidal silica, having dimensions not exceeding 5 micrometers; and—subjecting the so obtained mixture to mechanical processing by means of impacting-abrasive actions, until the aforesaid mass fraction is increased at least twice.

For the preparation of infusion solutions on the basis of using the inventive pharmaceutical composition, a single dose of the dry powder of antimicrobial preparation (soluble in the water for injection), indicated in the prescribing information, is dissolved in 10 ml of the water for injection, after which the whole volume of the derived solution is carried into the vial with the dry powder of the pharmaceutical composition indicated above, the same is intensively shaken for 2 or 3 minutes, after which the received suspension consisting of the solution of the antimicrobial preparation and the pharmaceutical composition is additionally dissolved in 50-100-200 ml of the 2% or 5% dextrose solution (depending of the composition contents) and is injected intravenously as an infusion according to the requirements indicated in the antimicrobial preparation prescribing information.

The therapeutic efficiency of antimicrobial preparations, when using the proposed pharmaceutical composition, is increased, if the obtained mixture (sodium chloride+colloidal silica or dextrose+colloidal silica) is subjected to mechanical impacting-abrasive actions so that the mass contents of colloidal silica particles, having dimensions not exceeding 5 micrometers, are at least 35%.

For the preparation of inventive pharmaceutical compositions we used crystalline powder of sodium chloride and dextrose crystalline powder, widely applicable in pharmacy, and provided by a Russian producer of pharmaceuticals "ABOLmed" LLC along with the antimicrobial preparations (amoxycillin+clavulanate, aztreonam, cefotaxime, ceftriaxone, ceftazidime, cefoperazone+sulbactam, cefepime, meropenem, am ikacin sulfate, azithromycin, vancomycin, capreomycin, fosfomycin and voriconazole). As colloidal silica we used the applicable in pharmacy AEROSIL® 200 (generic name: colloidal silica) produced by <<Evonik Degussa Corporation>> (Germany) consisting of round shape silica nanoparticles (average diameter of 7-40 nanometers) joined into non-regular microparticles having dimensions of less than 100 micrometers.

The choice of formulation of the inventive composition is grounded on a phenomenon of reciprocal sorption of molecules of antibacterial and antifungal preparations by nanoparticles and microparticles of colloidal silica, and a decrease of dimensions of colloidal silica microparticles in case of mechanical activation of its compounds with crystalline powder of sodium chloride and dextrose crystalline powder by means of intensive mechanical impacting-abrasive actions.

The introduction into the proposed compositions of the colloidal silica according to the provided weight ratio was defined experimentally on laboratory mice following the criterion of the maximum potentiating action onto the therapeutic efficiency of antimicrobial preparations with the minimum probability of the side effects emersion.

The claimed method for production of the pharmaceutical compositions indicated above by means of mechanical activation of the powder mixture of sodium chloride or glucose with colloidal silica by intensive mechanical rubbing impact allows, in comparison with other known means, for increasing the proportion of colloidal silica fine particles with a size not exceeding 5 micrometers at which molecules of antimicrobial preparations are adsorbed and actively phagocytized by macrophages [R18].

For this purpose the mixture of indicated agents (sodium chloride+colloidal silica or dextrose+colloidal silica) are subjected to mechanical activation by means of intensive mechanical impacting-abrasive actions until the weight ratio of the fine powder fraction (i.e. particles with a size not exciding 5 micrometers) of colloidal silica is increased at least twofold.

The so obtained powder pharmaceutical compositions are used for the production of infusion solutions consisting of colloidal silica fine particles with the molecules of various antimicrobial preparations inversely adsorbed on their surface, soluble in the sterile water for injections.

For obtaining the compositions a mechano-chemical approach was employed, comprising the treatment of solid ingredients of the mixture by an intensive mechanical impact, that is subjecting them to pressure and shearing obtained preferably in various grinders performing impacting-abrasive action on substances. The mixture of solid powder substances (sodium chloride+colloidal silica or dextrose+colloidal silica) is subjected to mechanical activation in drum mills. The used way of obtaining compounds allows for:

increasing the mass share of the most biologically active fine-dispersed fraction of cilica particles having dimensions not exceeding 5 micrometers; and achieving the full homogenicity of powder components in comparison with obtaining blends by simple mixture of components, or by vaporation of their solutions and, as a result, provides for the high pharmacological activity of the pharmaceutical composition.

As a quantitative criterion of the minimally required dose of mechanical action it is convenient to use the method of granulometry of the suspension of the obtained composition. Herein it is necessary that the weight content of colloidal silica particles not exceeding 5 um that may be measured by means of laser photometry, should increase at least twofold. The mechanical treatment of powder compounds is performed in rotary, vibratory or planetary mills. It is possible to use balls, pivots, etc. as grinding means.

The pharmacological trials of the obtained compositions on laboratory rodents (mice) have shown that the claimed composition produced by the claimed method has an express potentiating action onto therapeutic efficiency of antimicrobial (antibacterial and antifungal) preparations, when treating the bacterial sepsis induced by *Staphylococcus aureus*, *Escherichia coli* and *Pseudomonas aeruginosa*, as well as mycotic sepsis induced by *Candida albicans*, in comparison with usual solvents of antimicrobial medications.

Therefore the use of inventive pharmaceutical compositions and the production process thereof provide for the following advantages:

1) clinically significant increase of efficiency and quality of antimicrobial therapy of malignant contagious and inflammatory diseases, mortality decrease; and
2) ecological safety, wasteless and low-cost technology of pharmaceutical production.

DETAIL DESCRIPTION OF PREFERRED EMBODIMENTS OF THE INVENTION

While the invention may be susceptible to embodiment in different forms, there are described in detail herein below, specific embodiments of the present invention, with the understanding that the instant disclosure is to be considered an exemplification of the principles of the invention, and is not intended to limit the invention to that as described herein.

The present invention is illustrated by examples listed below.

Example 1

Solid Composition Production NaCl:Colloidal Silica.

A mixture of sodium chloride and colloidal silica in weight ratios of 4,5:1, 4,5:2, 4,5:5, 9:1, 9:2, and 9:5 is treated for 1, or 2, or 4 hours in a drum rotary mill.

Analysis of the granulometric content of water suspensions of initial colloidal silica particles, as well different variations of compositions with NaCl, was conducted on a laser analyzer of particle dimensions Microsizer-201a produced by <<VA Instalt>>, Russia. Powder, being analyzed, in an amount of from 1 g to 5 g was placed into a sample preparation module (a cuvet having a liquid volume of 150 cm$^3$) in a quantity sufficient for achieving 70-75% of optical transmission through the cuvet. After passing 1-2 minutes, a measurement was conducted with a simultaneous treatment of the suspension for destruction of agglomerations. The measurement data were processed according to a computer program embedded into the analyzer. The obtained measurement results were presented in the form of hystograms for weight distribution by particle dimensions.

For determining the number of antimicrobial preparations sorbed by colloidal silica particles, 0.5 g antibiotic substance (by active matter) was dissolved in 5 cm$^3$ water for injections. Thereafter, the known quantity of dry compositions NaCl:Colloidal silica suspended in the fresh antibiotic solution, the obtained suspension was centrifuges within 30 minutes at a speed of 12000 rpm, the supernatant liquid was poured carefully out, the residual matter of Colloidal silica was suspended again in the same quantity of water for injections. The concentration of antibiotic desorbing into the aqueous phase was determined by the HPLC method. Thereafter, the procedure of subsidence and suspending was repeated. The quantity of absorbed antibiotic was calculated based on the total antibiotic quantity desorbed from colloidal silica residual.

Data obtained for the granulometric composition and sorption rate are shown in Table 1 below. As it follows from the obtained data, the chosen conditions for producing the inventive composition allow for: —increasing a proportion of the fine powder fraction (with a particles' dimensions not exceeding 5 micrometers) of colloidal silica at least twofold, and—attaining a binding degree of molecules of antimicrobial preparations by colloidal silica particles of at least 40%.

TABLE 1

Granulometric data of water suspensions of composition and solution of antimicrobial preparations produced on the basis of the composition application; the preparations' sorption rate by colloidal silica particles

| Composition content and contents of antimicrobial preparations solutions | Dimension and content % of colloidal silica particles % ≤5 um | Antimicrobial preparation sorption rate by colloidal silica particles (%) |
|---|---|---|
| Initial Colloidal silica | 15.2 | — |
| NaCl:Colloidal silica (4.5:1; mechanical activation 1 hour) | 38.5 | — |
| NaCl:Colloidal silica (4.5:2; mechanical activation 2 hours) | 41.3 | — |
| NaCl:Colloidal silica (4.5:5; mechanical activation 4 hours) | 39.2 | — |
| NaCl:Colloidal silica (9:1; mechanical activation 1 hour) | 37.7 | — |
| NaCl:Colloidal silica (9:2; mechanical activation 2 hours) | 43.9 | — |
| NaCl:Colloidal silica (9:5; mechanical activation 4 hours) | 35.8 | — |
| Ceftriaxone/NaCl:Colloidal silica (4.5:1; mechanical activation 1 hour) | 43.5 | 45.3 |
| Ceftriaxone/NaCl:Colloidal silica (4.5:2; mechanical activation 2 hours) | 45.4 | 47.8 |
| Ceftriaxone/NaCl:Colloidal silica (4.5:5; mechanical activation 4 hours) | 42.1 | 49.5 |
| Cefotaxime/NaCl:Colloidal silica (9:1; mechanical activation 1 hour) | 37.8 | 41.6 |
| Cefotaxime/NaCl:Colloidal silica (9:2; mechanical activation 2 hours) | 41.2 | 51.4 |
| Ceftazidime/NaCl:Colloidal silica (9:5; mechanical activation 2 hours) | 36.7 | 46.3 |
| Cefepime/NaCl:Colloidal silica (9:2; mechanical activation 2 hours) | 38.3 | 44.5 |
| Amikacin sulfate/NaCl:Colloidal silica (9:2; mechanical activation 2 hours) | 40.2 | 43.7 |
| Azithromycin/NaCl:Colloidal silica (9:2; mechanical activation 2 hours) | 39.1 | 51.9 |
| Vancomycin/NaCl:Colloidal silica (9:5; mechanical activation 2 hours) | 42.9 | 50.6 |
| Meropenem/NaCl:Colloidal silica (9:2; mechanical activation 2 hours) | 36.7 | 43.9 |

TABLE 1-continued

Granulometric data of water suspensions of composition and solution of antimicrobial preparations produced on the basis of the composition application; the preparations' sorption rate by colloidal silica particles

| Composition content and contents of antimicrobial preparations solutions | Dimension and content % of colloidal silica particles % ≤5 um | Antimicrobial preparation sorption rate by colloidal silica particles (%) |
|---|---|---|
| Voriconazole/NaCl:Colloidal silica (9:2; mechanical activation 2 hours) | 37.5 | 41.7 |
| Capreomycin/NaCl:Colloidal silica (9:5; mechanical activation 2 hours) | 40.1 | 49.9 |

Example 2

Obtaining Solid Composition.

Dextrose:Colloidal silica. A mixture of dextrose and colloidal silica in weight ratios of 20:1, 20:2, 20:5, 50:1, 50:2, and 50:5 is treated for 1, or 2, or 4 hours in a drum rotary mill.

Measurements of the granulometric content of water suspensions including colloidal silica and measurements of a sorption rate of antibiotics were performed following the methods described above in Example 1. Data obtained from the measurements are shown in Table 2. It follows from the data that the claimed method for preparation of the inventive composition also allows for: at least a double increase of a proportion of the fine powder fraction (having particles with dimensions not exceeding 5 micrometers) of colloidal silica and attaining the binding degree of antimicrobial preparations molecules by colloidal silica particles of at least 40%.

TABLE 2

Granulometric data of water suspensions of composition and solutions of antimicrobial preparations produced on the basis of the composition application; the preparations' sorption rate by colloidal silica particles

| Composition content and contents of antimicrobial preparations solutions | Dimension and content % of colloidal silica particles % ≤5 um | Antimicrobial preparation sorption rate by colloidal silica particles (%) |
|---|---|---|
| Initial Colloidal silica | 15.2 | — |
| Dextrose:Colloidal silica (20:1; mechanical activation 1 hour) | 39.1 | — |
| Dextrose:Colloidal silica (20:2; mechanical activation 2 hours) | 42.3 | — |
| Dextrose:Colloidal silica (20:5; mechanical activation 4 hours) | 41.2 | — |
| Dextrose:Colloidal silica (50:1; mechanical activation 1 hour) | 42.7 | — |
| Dextrose:Colloidal silica (50:2; mechanical activation 2 hours) | 39.9 | — |
| Dextrose:Colloidal silica (50:5; mechanical activation 4 hours) | 40.7 | — |
| Ceftriaxone/Dextrose:Colloidal silica (20:1; mechanical activation 1 hour) | 43.5 | 41.3 |
| Ceftriaxone/Dextrose:Colloidal silica (20:2; mechanical activation 2 hours) | 48.4 | 47.8 |
| Ceftriaxone/Dextrose:Colloidal silica (20:5; mechanical activation 4 hours) | 42.1 | 51.5 |
| Cefotaxime/Dextrose:Colloidal silica (50:1; mechanical activation 1 hour) | 41.8 | 40.6 |
| Cefotaxime/Dextrose:Colloidal silica (50:2; mechanical activation 2 hours) | 44.2 | 51.4 |

TABLE 2-continued

Granulometric data of water suspensions of composition and solutions of antimicrobial preparations produced on the basis of the composition application; the preparations' sorption rate by colloidal silica particles

| Composition content and contents of antimicrobial preparations solutions | Dimension and content % of colloidal silica particles % ≤5 um | Antimicrobial preparation sorption rate by colloidal silica particles (%) |
|---|---|---|
| Cefotaxime/Dextrose:Colloidal silica (50:5; mechanical activation 4 hours) | 46.7 | 66.3 |
| Ceftazidime/Dextrose:Colloidal silica (50:2; mechanical activation 2 hours) | 37.9 | 47.8 |
| Cefepime/Dextrose:Colloidal silica (50:2; mechanical activation 2 hours) | 42.1 | 44.9 |
| Azithromycin/Dextrose:Colloidal silica (50:2; mechanical activation 2 hours) | 41.8 | 55.7 |
| Vancomycin/Dextrose:Colloidal silica (50:5; mechanical activation 2 hours) | 36.9 | 50.9 |
| Meropenem/Dextrose:Colloidal silica (50:2; mechanical activation 2 hours) | 40.5 | 78.5 |
| Voriconazole/Dextrose:Colloidal silica (50:2; mechanical activation 2 hours) | 35.1 | 47.1 |
| Amikacin sulfate/Dextrose:Colloidal silica (50:2; mechanical activation 2 hours) | 43.6 | 52.3 |

Example 3

Determination of Therapeutic Efficiency of Antimicrobial Preparations, Wherein Solutions of the Antimicrobial Preparations for Intravenous Injection are Prepared Based on the Inventive Pharmaceutical Composition.

Research was carried out for beta-lactam antibiotics (amoxycillin+clavulanate, cefotaxime, ceftriaxone, cefoperazone+sulbactam, ceftazidime, cefepime, aztreonam, meropenem), of macrolides (azithromycin), of aminoglycosides (amikacin sulfate), of glycopeptides (vancomycin), of antifungal agent (voriconazole), as well as of fosfomycin.

Determination of therapeutic efficiency of antimicrobial agents was done on experimental models of sepsis and methods for statistical treatment of the obtained results ($\chi^2$) according to [R19 and R20].

Microgerms. *Staphylococcus aureus* (ATCC No 25923 F-49), *Escherichia coli* (ATCC No25922 F-50), *Pseudomonas aeruginosa* (ATCC No 27853 F-51), *Candida albicans* (ATCC No 24433).

Animals. The experiments were carried out on hybrid mice ($CBA\times C_{57}Black/_{6})CBF_1$ according to the "Regulations for test animals use" (USSR Ministry of health, order supplement No 755 from Dec. 8, 1977).

Experimental sepsis models. Tested mice were injected intravenously 0.8 ml of *P. aeruginosa* daily culture suspension with a dosage $5\times10^8$ CFU/mouse or *S. aureus* daily culture suspension with a dosage $10^{10}$ CFU/mouse or *E. coli* daily culture suspension with a dosage $8\times10^8$ CFU/mouse or *Candida albicans* daily culture suspension with a dosage $10^{10}$ CFU/mouse. Mice of a control group were injected the 0.9% solution of NaCl or 5% dextrose solution in the volume of 0.8 ml.

In a day after being infected, during 3 days, the tested mice were daily intravenously injected with the indicated above antimicrobial preparations, dissolved in 0.9% solution of NaCl or in 5% dextrose solution, as well as their solutions prepared based on the pharmaceutical composition (as described hereinabove).

All beta-lactams were injected daily in the amount of 0.2 mg/mouse, amikacin sulfate in the amount of 2 mg/mouse daily, vancomycin in the amount of 1 mg/mouse daily, fosfomycin in the amount of 2 mg/mouse daily, and voriconazole in the amount of 0.1 mg/mouse contained in 0.5 ml of solution. Following the same order, the control group was injected with 0.9% NaCl solution or 5% dextrose solution, as well as water solutions of the pharmaceutical composition in the volume of 0.5 ml.

The antibacterial therapy efficiency was evaluated based on the number of surviving mice on the seventh day after being infected [R19, R20].

The obtained data shown in Tables 3 and 4 reflect the results of three independent experiments (at least 30 test animals were used for research of each inventive pharmaceutical preparation).

TABLE 3

Bacterial sepsis antimicrobial therapy efficiency
(the preparation solutions have been prepared on the basis of composition NaCl:Colloidal silica)

| Tested antibiotics | Mice survival rate on the 7th day of infection * | | | | |
|---|---|---|---|---|---|
| | S. aureus | E. coli | P. aeruginosa | Candida albicans | $\chi^2$ |
| 0.9% NaCl solution | 0% (0/31) | 0% (0/30) | 0% (0/32) | 0% (0/30) | — |
| Solution NaCl:Colloidal silica (9:2; mechanical activation 2 hours) | 0% (0/30) | 0% (0/34) | 0% (0/32) | 0% (0/31) | — |
| Amoxycillin + clavulanate/0.9% NaCl solution | 40.0% (12/30) | 41.9% (13/31) | — | —** | $P < 0.01$ |
| Amoxycillin + clavulanate/NaCl:Colloidal silica (9:2; mechanical activation 2 hours) | 83.9% (26/31) | 83.3% (25/30) | — | — | |
| Cefotaxime/0.9% NaCl solution | 43.7% (14/32) | 37.5% (12/32) | — | — | $P < 0.01$ |
| Cefotaxime/NaCl:Colloidal silica (9:2; mechanical activation 2 hours) | 81.2% (26/32) | 86.7% (26/30) | — | — | |
| Cefoperazone + sulbactam/0.9% NaCl solution | 43.3% (13/30) | 59.3% (19/32) | 46.6% (14/30) | — | $P < 0.01$ |
| Cefoperazone + sulbactam/NaCl:Colloidal silica (9:2; mechanical activation 2 hours) | 80.6% (25/31) | 93.5% (29/31) | 93.3% (28/30) | — | |
| Ceftazidime/0.9% NaCl solution | 38.7% (12/31) | 48.4% (15/31) | 46.7% (14/30) | — | $P < 0.01$ |
| Ceftazidime/NaCl:Colloidal silica (9:2; mechanical activation 2 hours) | 78.1% (25/32) | 90.6% (29/32) | 87.0% (27/31) | — | |
| Cefepime/0.9% NaCl solution | 46.7% (14/30) | 58.1% (18/31) | 51.6% (16/31) | — | $P < 0.01$ |
| Cefepime/NaCl:Colloidal silica (9:2; mechanical activation 2 hours) | 83.3% (25/30) | 93.3% (28/30) | 90.0% (27/30) | — | |
| Aztreonam/0.9% NaCl solution | — | 70.0% (21/30) | 67.7% (21/31) | — | $P < 0.01$ |
| Aztreonam/NaCl:Colloidal silica (9:2; mechanical activation 2 hours) | — | 93.9% (31/33) | 90.3% (28/31) | — | |

TABLE 3-continued

Bacterial sepsis antimicrobial therapy efficiency
(the preparation solutions have been prepared on the basis of composition NaCl:Colloidal silica)

| Tested antibiotics | Mice survival rate on the 7th day of infection * | | | | |
|---|---|---|---|---|---|
| | S. aureus | E. coli | P. aeruginosa | Candida albicans | $\chi^2$ |
| Meropenem/0.9% NaCl solution | 70.9% (22/31) | 73.8% (31/42) | 71.8% (23/32) | — | $P < 0.01$ |
| Meropenem/NaCl:Colloidal silica (9:2; mechanical activation 2 hours) | 90.9% (30/33) | 95.2% (40/42) | 94.1% (32/34) | — | |
| Azithromycin/0.9% NaCl solution | 43.3% (13/30) | — | — | — | $P < 0.01$ |
| Azithromycin/NaCl:Colloidal silica (9:2; mechanical activation 2 hours) | 90.0% (27/30) | — | — | — | |
| Vancomycin/0.9% NaCl solution | 71.4% (30/42) | — | — | — | $P < 0.01$ |
| Vancomycin/NaCl:Colloidal silica (9:2; mechanical activation 2 hours) | 97.5% (39/40) | — | — | — | |
| Amikacin sulfate/0.9% NaCl solution | — | 48.3% (15/31) | — | — | $P < 0.01$ |
| Amikacin sulfate/NaCl:Colloidal silica (9:2; mechanical activation 2 hours) | — | 86.6% (26/30) | — | — | |
| Fosfomycin/0.9% NaCl solution | 36.7% (11/30) | 43.3 % (13/30) | 30.0% (9/30) | — | $P < 0.01$ |
| Fosfomycin/NaCl:Colloidal silica (9:2; mechanical activation 2 hours) | 83.3% (25/30) | 86.7% (26/30) | 61.3% (19/31) | — | |
| Voriconazole/0.9% NaCl solution | — | — | — | 45.1% (14/31) | $P < 0.01$ |
| Voriconazole/NaCl:Colloidal silica (9:2; mechanical activation 2 hours) | — | — | — | 90.3% (28/31) | |

* in % and absolute values (survival rate/infected animals).
**tests were not conducted

TABLE 4

Bacterial sepsis antimicrobial therapy efficiency
(the preparation solutions have been prepared on the basis of composition Dextrose:Colloidal silica)

| Tested antibiotics | Mice survival rate on the 7th day of infection * | | | | |
|---|---|---|---|---|---|
| | S. aureus | E. coli | P. aeruginosa | Candida albicans | $\chi^2$ |
| 5% dextrose solution | 0% (0/31) | 0% (0/30) | 0% (0/32) | 0% (0/30) | — |
| Solution Dextrose:Colloidal silica (50:2; mechanical activation 2 hours) | 0% (0/30) | 0% (0/31) | 0% (0/30) | 0% (0/30) | — |
| Ceftriaxone/5% dextrose solution | 40.6% (13/32) | 45.2% (14/31) | — | —** | $P < 0.01$ |
| Ceftriaxone/Dextrose:Colloidal silica (50:2; mechanical activation 2 hours) | 83.9% (26/31) | 90.0% (27/30) | — | — | |

TABLE 4-continued

Bacterial sepsis antimicrobial therapy efficiency
(the preparation solutions have been prepared on the basis of
composition Dextrose:Colloidal silica)

| Tested antibiotics | Mice survival rate on the 7th day of infection * | | | | |
|---|---|---|---|---|---|
| | S. aureus | E. coli | P. aeruginosa | Candida albicans | $\chi^2$ |
| Cefotaxime/5% dextrose solution | 42.8% (15/35) | 43.7% (14/32) | — | — | P < 0.01 |
| Cefotaxime/ Dextrose:Colloidal silica (50:2; mechanical activation 2 hours) | 84.4% (27/32) | 81.2% (26/32) | — | — | |
| Ceftazidime/5% dextrose solution | 40.0% (12/30) | 53.3% (16/30) | 46.8% (15/32) | — | P < 0.01 |
| Ceftazidime/ Dextrose:Colloidal silica (50:2; mechanical activation 2 hours) | 86.7% (26/30) | 93.3% (28/30) | 87.0% (27/31) | — | |
| Cefepime/5% dextrose solution | 56.7% (17/30) | 54.4% (17/31) | 50.0% (15/30) | — | P < 0.01 |
| Cefepime/ Dextrose:Colloidal silica (50:2; mechanical activation 2 hours) | 90.0% (27/30) | 93.7% (30/32) | 93.5% (29/31) | — | |
| Azithromycin/ 5% dextrose solution | 43.3% (13/30) | — | — | — | P < 0.01 |
| Azithromycin/ Dextrose:Colloidal silica (50:2; mechanical activation 2 hours) | 80.6% (25/31) | — | — | — | |
| Vancomycin/5% dextrose solution | 77.5% (31/40) | — | — | — | P < 0.01 |
| Vancomycin/ Dextrose:Colloidal silica (50:2; mechanical activation 2 hours) | 95.0% (38/40) | — | — | — | |
| Meropenem/5% dextrose solution | 73.8% (31/42) | 78.0% (32/41) | 74.4% (32/43) | — | P < 0.01 |
| Meropenem/ Dextrose:Colloidal silica (50:2; mechanical activation 2 hours) | 95.1% (39/41) | 95.0% (38/40) | 95.2% (40/42) | — | |
| Amikacin sulfate/5% dextrose solution | — | 46.7% (14/30) | — | — | P < 0.01 |
| Amikacin sulfate/ Dextrose:Colloidal silica (50:2; mechanical activation 2 hours) | — | 83.3% (25/30) | — | — | |
| Fosfomycin/5% dextrose solution | 43.7% (14/32) | 46.7% (14/30) | 35.2% (15/34) | — | P < 0.01 |
| Fosfomycin/ Dextrose:Colloidal silica (50:2; mechanical activation 2 hours) | 87.5% (28/32) | 90.0% (27/30) | 85.3% (29/34) | — | |
| Voriconazole/ 5% dextrose solution | — | — | — | 46.7% (14/30) | P < 0.01 |
| Voriconazole/ Dextrose:Colloidal silica (50:2; mechanical activation 2 hours) | — | — | — | 93.5% (29/31) | |

* in % and absolute values (survival rate/infected animals).
** tests were not conducted As it can be seen from Tables 3 and 4, all the inventive pharmaceutical compositions for preparing injections in all of the tested antimicrobial preparations containing the finely dispersed powder of nanostructured colloidal silica, fairly increase their therapeutic efficiency when treating overwhelming sepsis of tested animals, provoked by *Staphylococcus aureus, Escherichia coli, Pseudomonas aeruginosa* and *Candida albicans*.

Therefore, following the obtained data, a conclusion can be made that the inventive pharmaceutical compositions for preparing solutions of antibacterial and antifungal preparations for intravenous infusions (NaCl: Colloidal silica and Dextrose: Colloidal silica) have a significant clinically important potentiating impact on therapeutic efficiency thereof, when treating malignant contagious and inflammatory diseases, in comparison with traditional solvents (prototypes of the invention).

REFERENCES

R-1—Kucers' The use of antibiotics//By M. L. Grauson, S. M. Crowe, J. S. McCarthy et al. $6^{th}$ ed, 2 vols, 3000 pp. London, UK, Hodder Education/ASM Press, 2010.

R-2—Abeylath S. C., Turos E. Drug delivery approaches to overcome bacterial resistance to β-lactam antibiotics// Expert Opinion on Drug Delivery. —2008. —Vol. 5. —P. 931-949.

R-3—Bastus N. G., Sanchez-Tillo E., Pujals S. et al. Peptides conjugated to gold nanoparticles induce macrophage activation//Molecular Immunology. —2009. —Vol. 46. —P. 743-748.

R-4—Pinto-Alphandary H., Andremont A., Couvreur P. Targeted delivery of antibiotics using liposomes and nanoparticles: research and applications//International Journal of Antimicrobial Agents. —2000. —Vol. 13. —P. 155-168.

R-5—Ulbrich W., Lamprech A. Targeted drug-delivery approaches by nanoparticulate carriers in the therapy of inflammatory diseases//Journal Royal Society Interface. —2010. —Vol. 7, Suppl. 1. —P. S55-S66.

R-6—Rosemary M. J., MacLaren I., Pradeep T. Investigation of antibacterial properties of ciprofloxacin@SiO2.// Langmuir. —2006. —Vol. 22. —P. 10125-10129.

R-7—Rai A., Prabhune A., Perry C. C. Antibiotic mediated synthesis of gold nanoparticles with potent antimicrobial activity and their application in antimicrobial coatings// Journal of Materials Chemistry. —2010. —Vol. 20. —P. 6789-6798.

R-8—Zolnik B. S., Gonzalez-Fernandez A., Sadrieh N., Dobrovolskaia V. Minireview: Nanoparticles and the immune system//Endocrinology. —2010. —Vol. 151. —P. 458-465.

R-9—Pinto-Alphandary H., Balland O., Laurent M. et al. Intracellular visualization of ampicillin-loaded nanoparticles in peritoneal macrophages infected in vitro with *Salmonella typhimurium*//Pharmaceutical Research. —1994. —Vol. 11. —P. 38-46.

R-10—Park J-H., Gu L., Maltzahn G. et al. Biodegradable luminescent porous silicon nanoparticles for in vivo applications//Nature Materials. —2009. —Vol. 8. —P. 331-336.

R-11—Hetrick E. M., Shin J. H., Stasko N. A. et al. Bactericidal efficacy of nitric oxide-releasing silica nanoparticles//ACS Nano. —2008. —Vol. 2. —P. 235-246.

R-12—Pernis B. Silica and the immune system//Acta Biomed. —2005. —Vol. 76, Suppl. 2. —P. 38-44.

R-13—Tasciotti E., Liu X., Bhavane R. Et et al. Mesoporous silicon particles as a multistage delivery system for imaging and therapeutic applications//Nature Nanotechnology. —2008. —Vol. 3. —P. 151-157.

R-14—Seleem M. N., Munusamy P., Ranjan A et al. Silica-antibiotic hybrid nanoparticles for targeting intracellular pathogens//Antimicrobial Agents and Chemotherapy. —2009. —Vol. 53. —P. 4270-4274.

R-15—Chuiko A., Pentyuk A., Shtat'ko E., Chuiko N. Medical aspects of application of highly disperse amorphous silica//Surface Chemistry in Biomedical and Environmental Science.

Edited by J. P. Blitz and V. Gun'ko.II. Mathematics, Physics and Chemistry. —2006. —Vol. 228. —P. 191-204.

R-16—Waters K. M., Masiello L. M., Zangar R. C. et al. Macrophage responses to silica nanoparticles are highly conserved across particle sizes//Toxicological Sciences. —2009. —Vol. 107. —P. 553-569.

R-17—Lucarelli M., Gatti A. M., Savarino G. et al. Innate defence functions of macrophages can be biased by nano-sized ceramic and metallic particles//European Cytokine Network. —2004. —Vol. 15. —P. 339-346.

R-18—Hamilton R. F., Thakur S. A., Mayfair J. K., Holian A. MARCO mediates silica uptake and toxicity in alveolar macrophages from C57BL/6 mice//Journal Biological Chemistry. —2006. —Vol. 281. —P. 34218-34226.

R-19—Eckhardt C., Fickweiler K., Schaumann R. et al. Therapeutic efficacy of moxifloxacin in a murine model of severe systemic mixed infection with *E. coli* and *B. fragilis*//Anaerobe. —2003. —Vol. 9. —P. 157-160.

R-20—Schaumann R., Blatz R., Beer J. et al. Effect of moxifloxacin versus imipenem/cilastatin treatment on the mortality of mice infected intravenously with different strains of *Bacteroides fragilis* and *Escherichia coli*//Journal of Antimicrobial Chemotherapy. —2004. —Vol. 53. —P. 318-324.

We claim:

1. A method of making an injection pharmaceutical composition soluble in water, said method comprising the steps of:

(a) preparing a powder composition consisting of sodium chloride in a powder form and powdered silica nanoparticles having an average diameter of from 7-40 nm joined into microparticles having a size of less than 100 μm, wherein said sodium chloride and said powdered silica are present in said powder composition in a weight ratio of 4.5:1 to 4.5:5 or 9:1 to 9:5, and further wherein said powder composition has a mass fraction;

(b) subjecting said powder composition to intensive mechanical impact and abrasive action, so that at least 35% of said silica microparticles are reduced to dimensions not exceeding 5 micrometers, thereby increasing said mass fraction of said powder composition and producing a mechano-chemical activated powder composition;

c) selecting a single dose of a dry powder of a pharmaceutical agent soluble in water for injection, and dissolving said single dose in 10 ml of water, thereby obtaining a pharmaceutical solution;

d) mixing said pharmaceutical solution of step (c) with said mechano-chemical activated power composition of step (b), thereby obtaining a suspension;

e) shaking said suspension for 2-3 minutes to provide an injection pharmaceutical composition; and f) further dissolving said injection pharmaceutical composition in 50 to 200 ml of a 0.45% or 0.9% aqueous solution of sodium chloride, thereby obtaining a ready to use injection pharmaceutical composition.

* * * * *